(12) United States Patent
Bunker et al.

(10) Patent No.: US 7,576,320 B2
(45) Date of Patent: Aug. 18, 2009

(54) PHOTOELECTRIC ION SOURCE PHOTOCATHODE REGENERATION SYSTEM

(75) Inventors: Stephen N. Bunker, Wakefield, MA (US); Leonid Krasnobaev, Framingham, MA (US)

(73) Assignee: Implant Sciences Corporation, Wakefield, MA (US)

( * ) Notice: Subject to any disclaimer, the term of this patent is extended or adjusted under 35 U.S.C. 154(b) by 560 days.

(21) Appl. No.: 11/248,603

(22) Filed: Oct. 12, 2005
(Under 37 CFR 1.47)

(65) Prior Publication Data
US 2006/0214580 A1    Sep. 28, 2006

Related U.S. Application Data

(63) Continuation-in-part of application No. 10/890,820, filed on Jul. 14, 2004, now Pat. No. 7,098,672, which is a continuation-in-part of application No. 10/349,491, filed on Jan. 22, 2003, now Pat. No. 6,828,795, which is a continuation-in-part of application No. 10/295,039, filed on Nov. 14, 2002, now abandoned, and a continuation-in-part of application No. 10/295,010, filed on Nov. 14, 2002, now Pat. No. 6,861,646, application No. 11/248,603, and a continuation-in-part of application No. 10/853,563, filed on May 25, 2004, now Pat. No. 7,244,288, application No. 11/248,603, and a continuation-in-part of application No. 10/818,434, filed on Apr. 5, 2004, now Pat. No. 6,870,155, which is a continuation-in-part of application No. 10/295,010, filed on Nov. 14, 2002, now Pat. No. 6,861,646, said application No. 10/818,434 and a continuation-in-part of application No. 10/295,039, filed on Nov. 14, 2002, now abandoned, , said application No. 10/818,434 and a continuation-in-part of application No. 10/349,491, filed on Jan. 22, 2003, now Pat. No. 6,828,795, , said application No. 10/818,434 and a continuation-in-part of application No. 10/754,088, filed on Jan. 7, 2004, now Pat. No. 6,888,128.

(60) Provisional application No. 60/708,002, filed on Aug. 12, 2005, provisional application No. 60/357,394, filed on Feb. 15, 2002, provisional application No. 60/357,618, filed on Feb. 15, 2002, provisional application No. 60/363,485, filed on Mar. 12, 2002, provisional application No. 60/473,649, filed on May 28, 2003.

(51) Int. Cl.
    *H01J 49/10*    (2006.01)
(52) U.S. Cl. ............ 250/286; 250/287; 250/423 R; 250/423 P
(58) Field of Classification Search ......... 250/287, 250/288, 423 R, 424, 423 P, 427, 286
See application file for complete search history.

(56) References Cited

U.S. PATENT DOCUMENTS 4,476,392 A  *  10/1984  Young ............. 250/423 R

\* cited by examiner

*Primary Examiner*—Kiet T Nguyen (57) ABSTRACT

An explosive detection system based on an ion mobility spectrometer detects the presence of trace molecules in air. Such instruments require an ion source to ionize the trace molecules. An ion source that does not require a radioactive source to operate can use the photoelectric effect to produce electrons. Such a photoelectric ion source will gradually be contaminated and lose its photoelectron emission properties when operated in the air. The photocathode of the ion source can be automatically regenerated by a heater in thermal communication with the photocathode. The heater may be activated when the photoelectron emission falls below a predetermined value ro may run or cycle continuously.

19 Claims, 4 Drawing Sheets

PHOTOELECTRIC ION SOURCE PHOTOCATHODE REGENERATION SYSTEM

CROSS-REFERENCE TO RELATED APPLICATIONS

This application claims priority to U.S. provisional patent application No. 60/708,002 filed Aug. 12, 2005 and is a continuation-in-part of U.S. patent application Ser. No. 10/890,820 filed on Jul. 14, 2004 (now U.S. Pat. No. 7,098,672) which is a continuation-in-part of U.S. patent application Ser. No. 10/349,491 filed on Jan. 22, 2003 (now U.S. Pat. No. 6,828,795), which is a continuation-in-part of U.S. patent application Ser. No. 10/295,039 filed on Nov. 14, 2002 (now abandoned) and U.S. patent application Ser. No. 10/295,010 filed on Nov. 14, 2002 (now U.S. Pat. No. 6,861,646), both of which claim priority to U.S. provisional application No. 60/357,394, filed Feb. 15, 2002, U.S. provisional application No. 60/357,618, filed Feb. 15, 2002, and U.S. provisional application No. 60/363,485, filed Mar. 12, 2002, all of which are incorporated herein by reference. This application is also a continuation-in-part of U.S. patent application Ser. No. 10/853,563, filed May 25, 2004 (now U.S. Pat. No. 7,244,288), which claims priority from U.S. provisional patent Application No. 60/473,649, filed May 28, 2003, both of which are incorporated herein by reference. This application is also a continuation-in-part of U.S. patent application Ser. No. 10/818,434 filed on Apr. 5, 2004 (now U.S. Pat. No. 6,870,155) which is a continuation-in-part of U.S. patent application Ser. No. 10/295,010 filed on Nov. 14, 2002 (now U.S. Pat. No. 6,861,646), U.S. patent application Ser. No. 10/295,039 filed on Nov. 14, 2002 (now abandoned), U.S. patent application Ser. No. 10/349,491 filed on Jan. 22, 2003 (now U.S. Pat. No. 6,828,795), and U.S. patent application Ser. No. 10/754,088 filed on Jan. 7, 2004 (now U.S. Pat. No. 6,888,128), all of which are incorporated by reference herein and all of which claim priority, directly or through one or more parent applications, to U.S. Provisional Application No. 60/357,394, filed Feb. 15, 2002, U.S. Provisional Application No. 60/357,618, filed Feb. 15, 2002, and U.S. Provisional Application No. 60/363,485, filed Mar. 12, 2002, all of which are incorporated herein by reference.

BACKGROUND OF THE INVENTION

1. Field of the Invention

This invention relates to detection of explosives and more particularly to an ion source of an ion mobility spectrometry instrument that detects chemicals present as vapors in air or other gases, or liberated as vapors from condensed phases such as particles or solutions.

2. Description of Related Art

Ion mobility spectrometer (IMS) instruments operate on the basis of the time taken by ionized molecules to move through a gas-filled drift region to a current collector while under the influence of an electric field. The ions are typically created in an atmospheric pressure gas-filled chamber called the ion source, which is connected to a drift chamber through an orifice or a barrier grid. The ion source may use any of a variety of techniques to ionize atoms and molecules. One or more flowing streams of gas enter the ion source through one or more orifices, and the gas may exit through one or more different orifices. At least one of the flowing gas streams entering the ion source typically includes gas that has been sampled (the "sample gas") from the surrounding atmosphere or other source of vapor to be analyzed.

In some cases, the process of taking a sample begins with an operator rubbing an absorbent substance, such as chemical filter paper, onto the surface to be tested. Particles of the chemical of interest may then be transferred and concentrated on the absorber. This intermediate absorber is then brought to the vicinity of the sampling orifice of the IMS. The quantity of particles of the target substance on the target surface is usually very small, often corresponding to only nanograms or even picograms of particles per square centimeter. The IMS must be very sensitive to identify a valid signal from evaporated target molecules when the initial concentration and surface area of target particles is so small.

A sampling method that is employed is to provide a gas pump, which draws the sample gas into the ion source through a tube. For example, the pump may be disposed to provide a partial vacuum at the exit of the ion source. The partial vacuum is transmitted through the confines of the ion source and appears at the entrance orifice of the ion source. A further tubulation may be provided as an extension to a more conveniently disposed sampling orifice external to the IMS. The operator places a sample in the near vicinity of this external sampling orifice, and the ambient vapor is drawn into the gas flow moving towards the ion source.

The ion source of the IMS provides a cloud of charged particles that is approximately proportional to the concentration of target molecule vapor, as well as some other background molecules. This concentration is further dependent on the equilibrium vapor pressure of the target molecule, the temperature of the target molecule where it is emitting the vapor, the total flow rate of non-target gas that dilutes the target vapor, and possible adsorption losses on surfaces of the gas sampling system. Existing systems that utilize absorbent surface concentration sometimes employ an oven to greatly warm the absorbent material, often up to 200°, and thereby increase the target vapor concentration.

In some circumstances, it is desirable for IMS instruments to be able to sample vapors at a distance from the external sampling orifice. Examples may include, but not be limited to, sampling of vapor from complex surfaces that contain many holes, crevices, or deep depressions, textured materials such as cloth, people and animals that prefer not to be rubbed by absorbent material, large three dimensional objects, surfaces that must be sampled in a short time, and surfaces in which surface rubbing by human operators is inconvenient or expensive. In addition, it has been observed that the sampling orifice may become contaminated with vapor-emitting particles if the sample inadvertently contacts the orifice. Such contamination is particularly difficult to remove in a short period of time, thus preventing continuous operation of the instrument. Such contamination could be avoided if vapors are sampled at a distance from the sampling orifice.

The ion source found in the IMS is typically a radioactive beta source of nickel-63. The high energy beta particles have sufficient energy to ionize the surrounding gases. Other types of ion sources that have been reported include corona discharge, electric discharge, laser, x-ray, photoelectric effect, and short wavelength ultraviolet. The ion sources fall into two categories, those that produce relatively high energy electrons and those that produce relatively low energy electrons. The photoelectric effect and laser ion sources are in the latter category and thus are not as prone to decomposing delicate organic molecules.

The photoelectric effect is the emission of an electron from a surface that is induced by the absorption of a high energy photon, typically in the ultraviolet portion of the electromagnetic spectrum. This surface is called a photocathode. Typically, a solid electrically conducting surface, a semi-transparent electrically conducting surface, or an electrically conducting mesh is employed as the electron emitting surface. Another example that appears superficially similar to the corona source is a photocathode shaped like a needle or wire. In this case the photocathode is biased to a voltage that is not sufficient to induce significant corona emission but is dependent on photon absorption to emit electrons. The requirement for electrical conductivity is due to the surface charging that would occur for insulating surfaces. After an initial emission of electrons, subsequently emitted electrons would be attracted back to the original emitting surface due to the build-up of positive surface charge. Additionally, the electrically conducting surface must be in electrical communication with the destination for the emitted electrons in order to complete the circuit. Additionally, an ambient electric field is required to draw the emitted electrons away from the emitting surface, since their initial energy is very small, typically much less than 3 electron Volts, and they can readily be attracted back by even a small unbalanced residual positive charge on the emitting surface.

The electrons produced by the ion source readily combine with oxygen and other naturally occurring gases in the atmosphere. Alternatively, a special "reactant" gas species may be combined with the inflowing sample gas. The reactant gas may be selected for specific chemical and electron affinity properties in order to make the ion mobility spectrometer more sensitive or selective to specific chemical species. The electrically charged molecules, whether a naturally occurring gas or a special reactant gas, then transfer their charge by a variety of reactions to the target molecule of interest.

It is well known that a photocathode is sensitive to various forms of surface contamination, such as oxidation or coating. This can be particularly severe for an IMS, where the photocathode is operated at atmospheric pressure, rather than a vacuum. The gradual build up of contamination causes a gradual decrease in the emission of electrons, often by creating a barrier to passage of the lowest energy electrons in the emission spectrum or by creating a semi-insulating surface layer that retains positive charge long enough to inhibit electron emission.

A photoelectric effect ion source may be operated in continuous or pulsed modes. In pulsed mode an electric arc discharge flash lamp, such as a xenon flash lamp, may be employed as the source of ultraviolet (UV) photons. In continuous mode a short wavelength krypton, xenon, mercury, or deuterium arc lamp may be employed.

The ambient electric field required to draw the electrons from the photocathode is required only while the source of photons is in operation. After a sufficient delay to allow adequate separation of the electrons from the photocathode surface, the ambient electric field may be increased, decreased, or turned off as required for the desired operation of the ion mobility spectrometer.

SUMMARY OF THE INVENTION

According to the present invention, an ion mobility spectrometer includes a chamber, a photocathode and an anode that provide an electric field within said chamber, a source of ultraviolet wavelength photons in optical communication with the photocathode, a heater in thermal communication with said photocathode, and a temperature control system that raises the temperature of the photocathode independent of other heaters provided with said ion mobility spectrometer, whereby said dedicated heater provides regeneration and cleaning of said photocathode. A flow of gas through the chamber may include at least one chemical to be analyzed by the ion mobility spectrometer and the residue from the at least one chemical may be removed from said photocathode by said dedicated heater. The photocathode may have a surface that is electrically conductive. The surface may be a noble metal and/or a semiconductor. The surface may be a semi-transparent coating, a non-transparent coating, a solid plate, a needle, a wire, or a mesh. The surface may be mounted on an optically transparent window which may consist of sapphire, quartz, calcium fluoride, magnesium fluoride, or any other UV transparent material. The source of ultraviolet photons may be an arc discharge in an inert gas or a UV emitting light emitting diode (LED). The optical communication may be provided by one or more of an optically transparent window, a fiber optic, a mirror, an optical waveguide, and a lens. The anode may be charged to a voltage that is positive relative to the photocathode at least while the photocathode is illuminated with the ultraviolet wavelength photons. The dedicated heater may heat the photocathode to a temperature greater than 175 degrees centigrade. The heater may independently heat the photocathode to a temperature at least 50 degrees centigrade greater than the normal operating temperature of the ion mobility spectrometer in order to regenerate the photocathode. The independent temperature control system may be operated to heat the photocathode when the rate of photoelectron emission falls below a predetermined value. The heater may be any combination of a wire, heater tape, and conductive ink.

According further to the present invention, operating an ion mobility spectrometer includes providing sampling gas flow from an external gas sampling inlet of the ion mobility spectrometer proximal to an ion source, providing ultraviolet photons to a photocathode to emit electrons therefrom, accelerating electrons emitted from the photocathode using a voltage between an anode and the photocathode to produce ions, accelerating the ions through a drift tube to a current collector, measuring current reaching the current collector, and raising temperature of the photocathode independent of other heaters provided with the ion mobility spectrometer to provide regeneration and cleaning of the photocathode. The photocathode may be heated to a temperature greater than 175 degrees centigrade. The photocathode may be heated to a temperature at least 50 degrees centigrade greater than the normal operating temperature of the ion mobility spectrometer in order to regenerate the photocathode. Operating an ion mobility spectrometer may also include heating the photocathode when the rate of photoelectron emission falls below a predetermined value.

A photoelectric effect ion source is interfaced to an ion mobility spectrometer. The ultraviolet photon emissions to induce the emission of electrons may be provided by at least one of an electric arc discharge in an inert gas and a UV emitting light emitting diode. The source of photon emission may be at least one of: pulsed, keyed in a long pulse, and continuous. The source of photon emission may be separated from the photocathode surface by at least one of a window, a fiber optic, an optical waveguide or light guide, a mirror, a lens, and a semi-transparent grid. The photocathode surface may be a solid electrically conducting material, such as a metal or a semiconductor, a thin semi-transparent coating of an electrically conducting material, such as a metal or a semiconductor, an electrically conducting mesh made of a metal or a semiconductor, or a needle or wire made of a metal or a semiconductor.

A means for heating the photocathode is provided. The means for heating may be at least one of electrical resistance heating, chemical combustion heating, and photon energy absorption. The means may be operated continuously, pulsed, or keyed in a long pulse. The photocathode temperature obtained may be greater than 175° C.

An ambient electric field may be provided during the emission of the ultraviolet light onto the photocathode in order to assist in drawing the resultant electrons away from the photocathode. If the photon flux is pulsed, the ambient electric field may be maintained for a period of time after the photon flux of ultraviolet light has been terminated in order to allow the pulse of photo-induced electrons to separate by at least one millimeter from the photocathode. This time may be dependent on the strength of the ambient electric field and the mobility of the electrons in the ambient atmosphere.

The photocathode may be heated to a selected temperature continuously during operation of the IMS, and it may be specially heated to a higher temperature in order to regenerate or clean the photocathode to restore the electron emission to a standard level.

The photocathode may be an electrically conducting material, which may be either a metal or a semiconductor. The metal may be a noble metal, which does not readily oxidize over the temperature range of heating. The semiconductor may be a binary or trinary semiconductor that does not readily oxidize over the temperature range of heating.

The temperature of the photocathode during a regeneration cycle may be controlled either through a pre-determined calibration of heater Watts versus temperature or by a temperature controlled feedback loop that monitors a temperature sensor, such as a resistance temperature device (RTD), a thermocouple, or a thermistor. The feedback loop may be in the form of an electrical circuit or a software controlled system.

The maximum temperature of the photocathode during regeneration may be limited to a preset value that is consistent with maintaining the integrity of the photocathode surface. For the case of a semi-transparent photocathode, many desirable coating materials may be subject to thermally induced reformation of their morphology. In some cases, a uniform thin coating may coalesce into clusters or islands of atoms or molecules gradually over many thermal cycles, causing a slow deterioration in electron emission. The number of cycles before a given level of performance degradation occurs may be dependent on the maximum temperature of the regeneration cycle and the time at this temperature with lower temperature and time preferred. The rate of thermally induced reformation may also be dependent on the choice of photocathode material with more refractory materials having the lower rate. For example, a gold coating may reform more quickly than a platinum coating.

The maximum temperature may be set to be sufficient to remove any accumulated coating or oxidation on the photocathode. The total Joules expended to heat the photocathode may be minimized to conserve energy in a battery-operated instrument, and thus as much thermal insulation as is possible may be employed. Additionally, the mass of photocathode, any substrate, and the heater assembly may be minimized to permit rapid thermal cycling and energy conservation. It may not be a requirement to completely regenerate the photocathode to a pristine, original state. Some photocathode materials rapidly degrade in the rate of electron emission upon exposure to clean air when irradiated with UV photons, but this degradation may reach a limit of about 30% to 50% of the maximum emission after several minutes of operation. This "burned in" emission rate may be more stable than the pristine emission rate and may be more useful for use in an analytical instrument. Thus, it may not be necessary to regenerate the photocathode all the way to a pristine state, thus saving energy and causing less morphological degradation of the photocathode.

The spectral output of the ion mobility spectrometer, sometimes referred to as a plasmagram, may be monitored to determine when the photoelectron emission has fallen below a predetermined threshold level. At this time the heater may be activated and the photocathode regenerated. One method of monitoring the plasmagram is to add up, i.e., integrate, all of its output values within a fixed data collecting time period. This sum is proportional to the number of photoelectrons produced by the photocathode. A target range of the sum or integral for acceptable operation may be selected.

Note that the system described herein may use negative ions or positive ions. The positions of the anode and cathode may be reversed from that disclosed herein to permit operation with positive ion species in which the electrons produced by the photocathode may be accelerated to sufficient voltage to positively ionize target molecules or intermediate reactant molecules.

BRIEF DESCRIPTION OF THE DRAWING

The invention is described with reference to the several figures of the drawing, in which.

DETAILED DESCRIPTION

Figure 1:
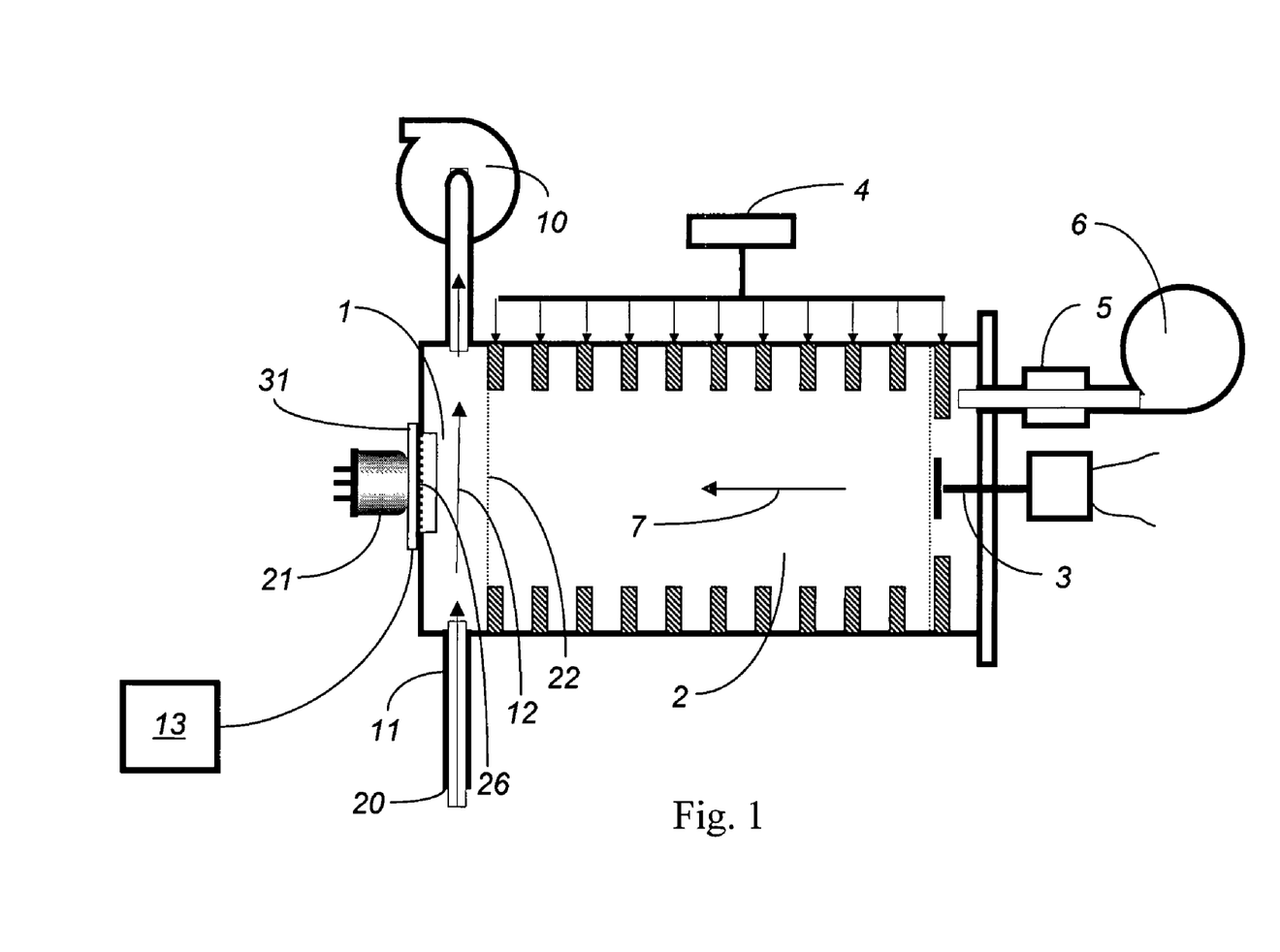
FIG. 1 is a schematic of a negative ion IMS detector that may be used in connection with the system described herein.

Referring to FIG. 1, an explosive detection system according to an embodiment of the system described herein uses an Ion Mobility Spectrometer (IMS) that senses negative ions. While any number of a variety of other embodiments may be used, the embodiment illustrated in FIG. 1 includes an ion source 1, a drift tube 2, a current collector 3, a source of negative operating voltage 4 and a source of purified drift gas 5, possibly having gas pump 6 associated therewith. An explosive detection system may also have a gas pump 10 for gas sampling and a tubular connection 11 between the ion source 1 and an external gas sampling inlet 20 that includes an orifice. Gas flow for drift gas 7 moves through the drift tube 2. A sampling gas flow 12 moves from the external gas sampling inlet 20 through the tubular connection 11 and ion source 1 to the gas pump 10. The ion source 1 may include of an optically transparent window 31 through which ultraviolet photons from a flash lamp 21 may pass to a semi-transparent photocathode 26. The photons may be generated by an arc discharge in an inert gas. The optically transparent window 31 may be made of sapphire, quartz, or any other appropriate material. Electrons emitted from the photocathode 26 are accelerated by a voltage between an anode 22 and the photocathode 26. The photocathode 26 may be electrically connected to the negative operating voltage 4. The electrons interact with gas within the ion source to produce ions that are accelerated through the drift tube 2 to the current collector 3, which completes the electrical circuit. The current reaching the current collector 3 is amplified to produce a drift time spectrum or plasmagram.

The explosive detection system of FIG. 1 may be used to sample gas proximal to different areas of a person without having any part of the explosive detection system touch the person. The explosive detection system of FIG. 1 may also be used to sample gas proximal to packages, luggage, etc. As described herein, features of the explosive detection system facilitate detection of chemicals associated with explosives in an unobtrusive manner.

The photocathode 26 has a surface portion and a substrate portion where the surface portion generates (emits) electrons while the substrate portion supports the surface. Thus, the photocathode 26 could be a single solid material or could have a first material or combination of materials at the surface where the electrons are generated (emitted) and a second material or combination of materials attached to and supporting the surface (e.g., beneath the surface). The surface of the photocathode 26 may be a semitransparent coating, a non-transparent coating, a solid plate, a mesh, a needle, or a wire.

For the system described herein, the photocathode 26 is heated using, for example, a heater (not shown in FIG. 1) controlled by an independent temperature control system 13. The independent temperature control system 13 may be implemented using conventional electronic components appropriate to the type of heater that is used and the desired temperature operating range. The photocathode 26 may be heated continuously, near continuously, or on any appropriate cycle. Heating the photocathode 26 during operation of the IMS facilitates regeneration or cleaning of the photocathode 26 to restore the electron emission to a standard level. In some embodiments, the photocathode 26 may be subject to relatively high heating when the rate of photoelectron emission of the photocathode 26 falls below a predetermined value.

Figures 2A, 2B, 2C, 2D:
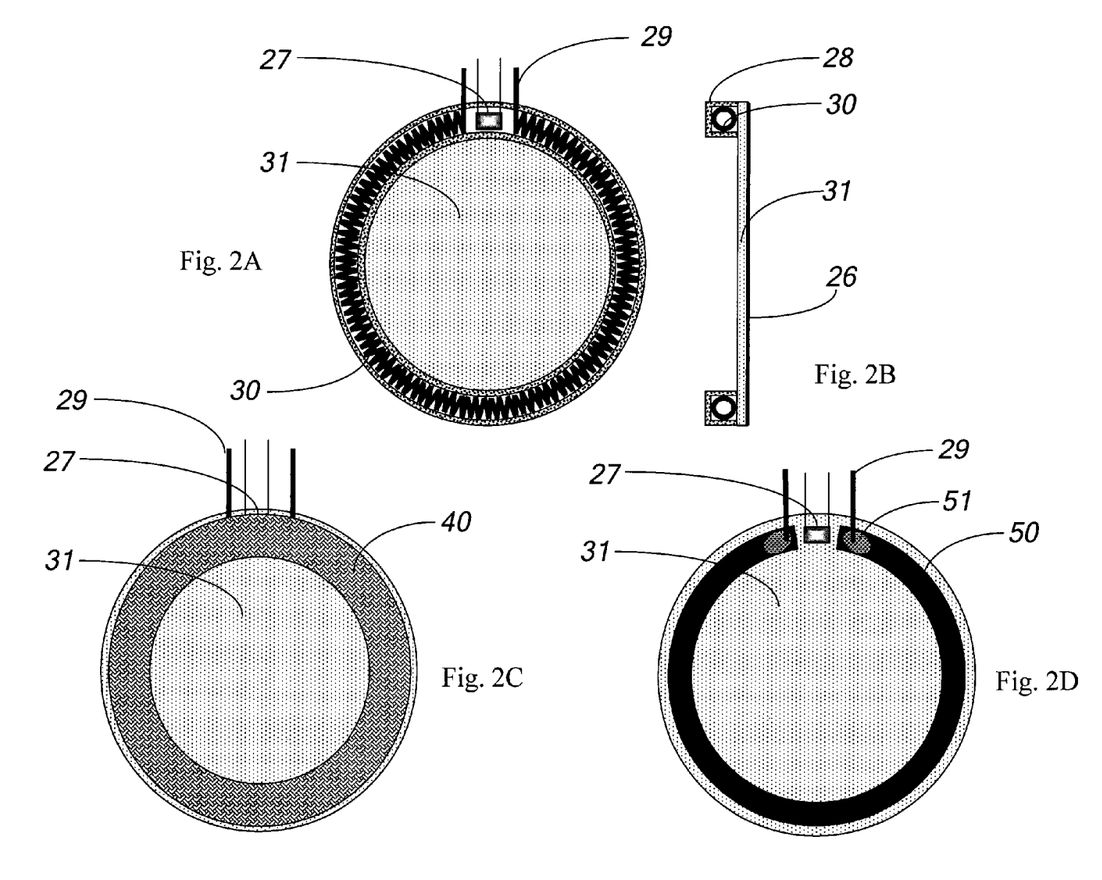
FIGS. 2A and 2B are schematic diagrams showing a possible embodiment for a photocathode heating unit that uses an electrically heated coil of wire mounted to a substrate that is in thermal connection with the photocathode.
FIG. 2C is a schematic diagram showing another possible embodiment for a photocathode heating unit that uses a heater tape mounted to a substrate that is in thermal connection with the photocathode.
FIG. 2D is a schematic diagram showing another possible embodiment for a photocathode heating unit that uses a resistive ink that is braised or fused to the substrate that is in thermal connection with the photocathode.

FIGS. 2A-2D show different embodiments for a photocathode heating element, provided proximal to the ion source 1, which heats the surface of the photocathode 26 in conjunction with the gas sampling system of the explosive detection system described herein. In FIG. 2A and FIG. 2B, the technique for heating is an electrically heated wire 30. The coil of heated wire 30 is disposed at or near the surface of the photocathode 26. The wire 30 may be provided by, or in connection with, an electrically conductive coating on the optically transparent window 31. The wire 30 and corresponding electrical leads 29 may be disposed within a clamping and containment chamber 28 (shown in FIG. 2B). The chamber 28 may be made from an electrically insulating material to avoid shorting out the wire 30. The wire 30 may be fabricated from a variety of low oxidation resistive alloys, such as Nichrome. The temperature of the photocathode 26 and/or the substrate may optionally be monitored using a temperature sensing device 27 that is mounted on the substrate and/or the photocathode 26. The temperature sensing device 27 may provide data to the independent temperature control system 13 (not shown in FIG. 2A). The temperature sensing device 27 may be an RTD, a thermocouple, a thermistor or any other appropriate device or combination of devices. All of the materials of these several components may be selected to withstand the desired photocathode regeneration temperature without rapid deterioration due to oxidation. Thermal insulation may be optionally added anywhere in the structure that does not appreciably interfere with the transmission of the UV photons or photoelectrons or the operation of the ion source in the IMS.

In FIG. 2C, an electrically heated heater tape 40 is shown as being used to heat the photocathode 26. The heater tape 40 may be disposed at or near the surface of the photocathode 26. The heater tape 40 may be an electrically conductive coating on the optically transparent window 31. The heater tape 40 may be disposed on the substrate of the photocathode 26, or on the photocathode 26 itself. The photocathode 26 and/or the substrate thereof may be embedded in an electrically insulating material to avoid shorting out the heating element within. The heater tape 40 may be fabricated from a variety of materials, such as polyimide foil or silicone. The heater tape 40 and corresponding electrical leads 29 may be clamped or glued to the substrate of the photocathode 26 and/or the optically transparent window 31. The temperature of the photocathode 26 and/or the substrate of the photocathode 26 may optionally be monitored using a temperature sensing device 27 mounted thereon. The temperature sensing device 27 may provide data to the independent temperature control system 13 (not shown in FIG. 2C). The temperature sensing device 27 may be an RTD, a thermocouple, a thermistor or any other appropriate device or combination of devices. All of the materials of these several components may be selected to withstand the desired photocathode regeneration temperature without rapid deterioration due to oxidation. Thermal insulation may be optionally added anywhere in the structure that does not appreciably interfere with the transmission of the UV photons or photoelectrons or the operation of the ion source in the IMS.

In FIG. 2D, a braised or fused conductive ink 50 is shown as being used for heating. The fused ink 50 may be disposed at or near the surface of the photocathode 26, on the optically transparent window 31, or the substrate of the photocathode 26. The fused ink 50 may be fabricated from a variety of materials, including, without limitation, a suspension of noble metal or near noble metal particles of various sizes in a carrier. The fused inks may be a mixture of palladium, silver, and glass frits that are commercially available, for example, as a number of varieties of resistor paste from Dupont, such as resistor paste formulation 0060A. Upon heating to a temperature in the range between six hundred and one thousand degrees Centigrade, the fused ink 50 may become braised onto the substrate of the photocathode 26. Electrical leads 51 may then be added to make contact to the fused ink 50. The temperature of the photocathode 26 and/or the substrate of the photocathode 26 may optionally be monitored using a temperature sensing device 27 mounted thereon. The temperature sensing device 27 may provide data to the independent temperature control system 13 (not shown in FIG. 2D). The temperature sensing device 27 may be an RTD, a thermocouple, a thermistor or any other appropriate device or combination of devices. All of the materials of these several components may be selected to withstand the desired photocathode regeneration temperature without rapid deterioration due to oxidation. Thermal insulation may be optionally added anywhere in the structure that does not appreciably interfere with the transmission of the UV photons or photoelectrons or the operation of the ion source in the IMS.

Figure 3:
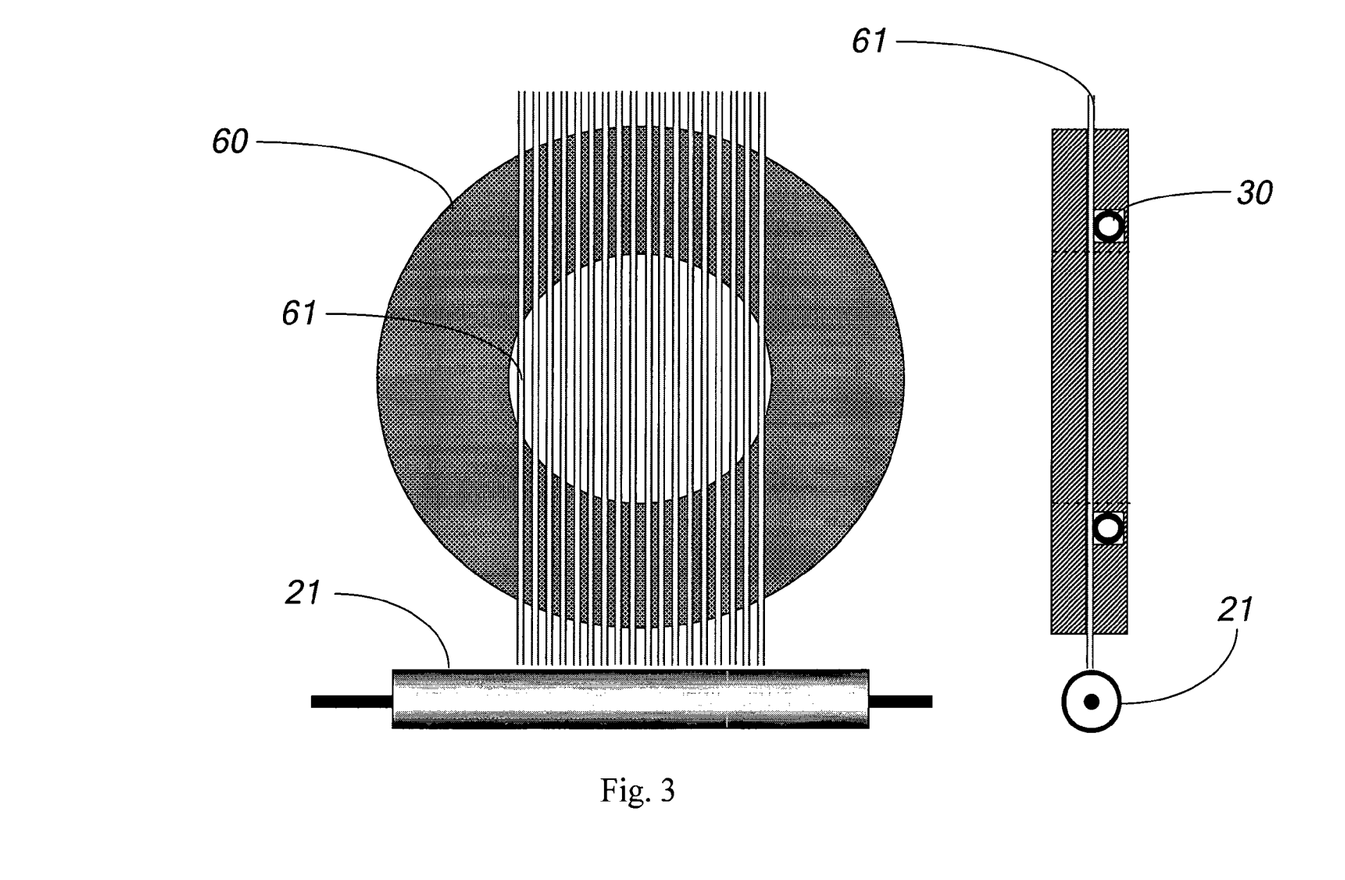
FIG. 3 is a schematic diagram illustrating a plurality of photocathodes made from a fiber optic substrate on which a semitransparent electrically conducting photocathode is coated according to an embodiment of the system described herein.

FIG. 3 is a schematic of a plurality of photocathodes 61 that use fiber optic substrates on which semitransparent electrically conducting photocathodes 61 are coated. Ultraviolet photons from the flash lamp 21 pass through the plurality photocathodes 61 and corresponding fiber optic substrates and reflect from the inside surface. The photons partially penetrate the semitransparent photocathodes 61, and photoelectrons are emitted. The fibers may be mounted onto an electrically conducting substrate 60, which contains an independently controlled heater 30. The independently controlled heater 30 may optionally be mounted external to the electrically conducting substrate 60. This photocathode geometry is useful for operation of the IMS for positive ions as well as negative ions.

Figure 4:
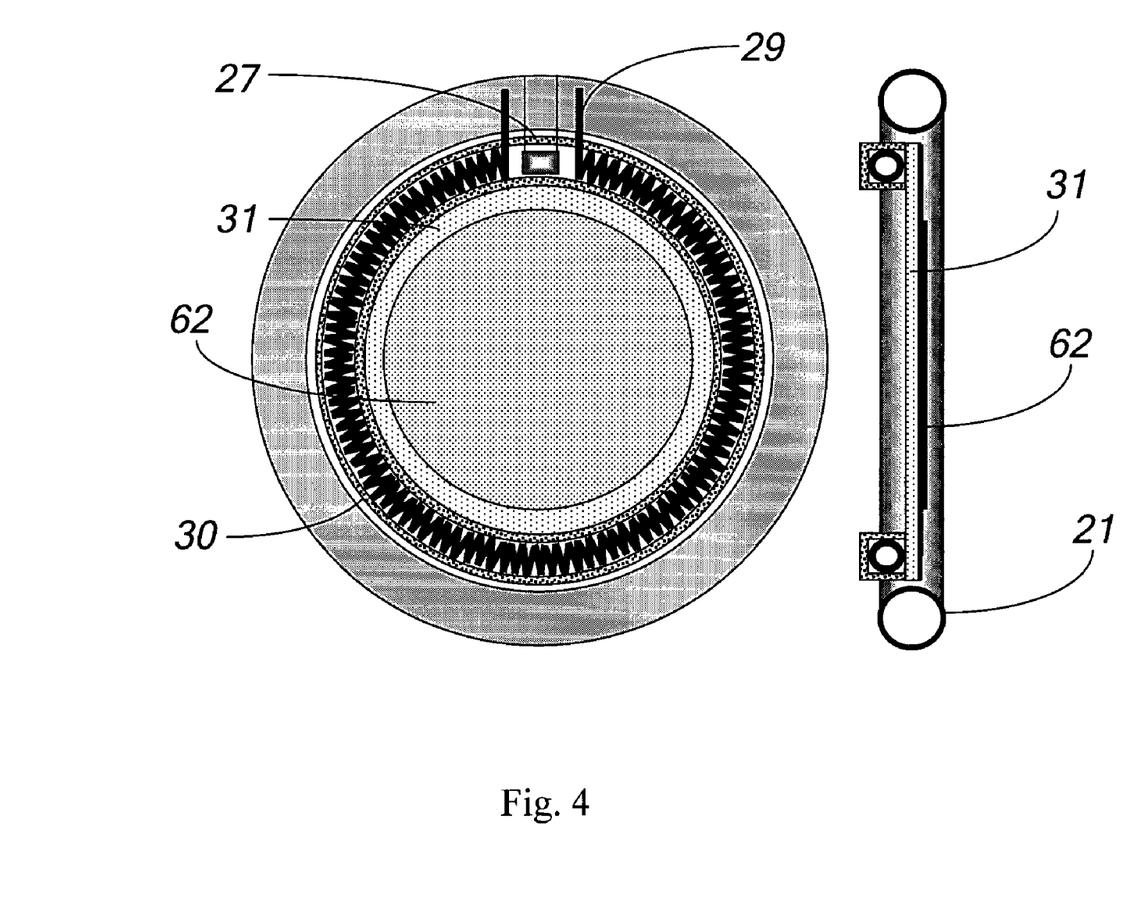
FIG. 4 is a schematic diagram illustrating a photocathode made from a coated fiber optic or optical waveguide according to an embodiment of the system described herein.

FIG. 4 shows another variation on the principle of the photocathode made from a coated fiber optic or optical waveguide. Here the optically transparent window 31 is illuminated through its rim by the flash lamp 21, and the ultraviolet photons are guided through the disk by the opposing flat face surfaces. A photocathode is provided by a semitransparent coating 62 on the surface of the optically transparent window 31. The interaction of photons is similar to that of FIG. 3, except that in this case the optically transparent window 31 is a continuous solid surface, rather than a plurality of fibers. A heater 63 may be mounted directly on the optically transparent window 31. This geometry may be more suitable for generating negative ions in an IMS.

Note that, as illustrated by the embodiments of FIG. 3 and FIG. 4, optical communication between the photon source and the photocathode can be any one of a variety of appropriate mediums, including, without limitation, an optically transparent window, a fiber optic, a mirror, an optical waveguide, and a lens.

In an embodiment herein, the photocathode 26 may be heated (e.g., by the independent temperature control system 13) to a temperature greater than 175 degrees centigrade. Also, in an embodiment herein, the photocathode 26 may be heated to a temperature that is at least fifty degrees centigrade greater than the normal operating temperature of the ion mobility spectrometer in order to regenerate the photocathode 26.

The photocathode heating system for explosive detection systems described herein may incorporate other features, alone or in any combination, including without limitation features described in commonly assigned U.S. patents U.S. Pat. Nos. 6,828,795, 6,861,646, and 6,888,128, U.S. patent application Ser. No. 10/890,820, Ser. No. 10/295,039, Ser. No. 10/853,563, and Ser. No. 10/818,434, and U.S. provisional applications 60/357,394, 60/357,618, 60/363,485, and 60/473,649.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An ion mobility spectrometer, comprising:
    a chamber;
    a photocathode and an anode that provide an electric field within said chamber;
    a source of ultraviolet wavelength photons in optical communication with said photocathode;
    a heater in thermal communication with said photocathode; and
    a temperature control system that raises the temperature of the photocathode independent of any other heaters provided with said ion mobility spectrometer, whereby said heater in thermal communication with said photocathode provides regeneration and cleaning of said photocathode.

2. An ion mobility spectrometer, according to claim 1, wherein a flow of gas through said chamber includes at least one chemical to be analyzed by said ion mobility spectrometer and wherein residue from said at least one chemical is removed from said photocathode by said heater.

3. An ion mobility spectrometer, according to claim 1, wherein said photocathode has a surface that is electrically conductive.

4. An ion mobility spectrometer, according to claim 3, wherein said surface is at least one of: a noble metal and a semiconductor.

5. An ion mobility spectrometer, according to claim 3, wherein said photocathode surface is at least one of: a semitransparent coating, a non-transparent coating, a solid plate, a needle, a wire, and a mesh.

6. An ion mobility spectrometer, according to claim 5, wherein said surface is mounted on an optically transparent window.

7. An ion mobility spectrometer, according to claim 6, wherein said optically transparent window consists of a material selected from one of: sapphire, quartz, calcium fluoride, and magnesium fluoride.

8. An ion mobility spectrometer, according to claim 1, wherein said source of ultraviolet photons is selected from one of: an arc discharge in an inert gas and an ultraviolet emitting light emitting diode.

9. An ion mobility spectrometer, according to claim 1, wherein said optical communication is provided by at least one of an optically transparent window, a fiber optic, a mirror, an optical waveguide, and a lens.

10. An ion mobility spectrometer, according to claim 1, wherein said anode is charged to a voltage that is positive relative to said photocathode at least while said photocathode is illuminated with said ultraviolet wavelength photons.

11. An ion mobility spectrometer, according to claim 1, wherein said heater heats said photocathode to a temperature greater than 175 degrees centigrade.

12. An ion mobility spectrometer, according to claim 1, wherein said heater independently heats said photocathode to a temperature at least 50 degrees centigrade greater than the normal operating temperature of said ion mobility spectrometer in order to regenerate the photocathode.

13. An ion mobility spectrometer, according to claim 1, wherein said independent temperature control system is operated to heat said photocathode in response to the rate of photoelectron emission falling below a predetermined value.

14. An ion mobility spectrometer, according to claim 1, wherein the heater is a wire.

15. An ion mobility spectrometer, according to claim 1, wherein the heater uses heater tape.

16. An ion mobility spectrometer, according to claim 1, wherein the heater uses conductive ink.

17. A method of operating an ion mobility spectrometer, comprising:
    providing sampling gas flow from an external gas sampling inlet of the ion mobility spectrometer proximal to an ion source;
    providing ultraviolet photons to a photocathode to emit electrons therefrom;
    accelerating electrons emitted from the photocathode using a voltage between an anode and the photocathode in order to produce ions therefrom;
    accelerating ions through a drift tube to a current collector;
    measuring current reaching the current collector; and raising the temperature of the photocathode independent of any other heaters provided with the ion mobility spectrometer to provide regeneration and cleaning of the photocathode in response to the rate of photoelectron emission falling below a predetermined value.

18. A method, according to claim 17, further comprising:
heating the photocathode to a temperature greater than 175 degrees centigrade.

19. A method, according to claim 17, further comprising:
heating the photocathode to a temperature at least 50 degrees centigrade greater than the normal operating temperature of the ion mobility spectrometer in order to regenerate the photocathode.

* * * * *

UNITED STATES PATENT AND TRADEMARK OFFICE
CERTIFICATE OF CORRECTION

PATENT NO.        : 7,576,320 B2
APPLICATION NO.   : 11/248603
DATED             : August 18, 2009
INVENTOR(S)       : Bunker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 658 days.

Signed and Sealed this

Seventh Day of September, 2010

David J. Kappos
*Director of the United States Patent and Trademark Office*